United States Patent [19]

Vetter et al.

[11] Patent Number: 5,185,985
[45] Date of Patent: Feb. 16, 1993

[54] APPARATUS FOR HANDLING SYRINGE BODIES

[75] Inventors: Helmut Vetter, Ravensburg; Peter Geprägs, Weingarten, both of Fed. Rep. of Germany

[73] Assignee: Arzneimittel GmbH Apotheker Vetter & Co. Ravensburg, Ravensburg, Fed. Rep. of Germany

[21] Appl. No.: 720,902

[22] Filed: Jun. 25, 1991

[30] Foreign Application Priority Data

Jul. 9, 1990 [DE] Fed. Rep. of Germany ....... 4021836

[51] Int. Cl.$^5$ .............................................. B65B 7/28
[52] U.S. Cl. ........................................ 53/299; 53/328;
141/372; 206/560; 206/563; 211/71
[58] Field of Search ................ 53/281, 299, 319, 328;
141/165, 368, 372; 206/560, 562, 563; 211/4, 71

[56] References Cited

U.S. PATENT DOCUMENTS

| | | | |
|---|---|---|---|
| 959,038 | 5/1910 | Yard | 53/299 |
| 1,047,366 | 12/1912 | Alston | 211/4 |
| 3,390,783 | 7/1968 | Quackenbush, Jr. | 206/562 X |
| 4,256,153 | 3/1981 | Lamaziere | 211/71 X |
| 4,599,314 | 7/1986 | Shami | 206/563 X |
| 4,729,208 | 3/1988 | Galy et al. | 53/328 X |
| 4,774,772 | 10/1988 | Vetter et al. | 211/69 X |
| 4,880,122 | 11/1989 | Martindell | 211/4 X |
| 5,004,103 | 4/1991 | Connors et al. | 206/563 X |

Primary Examiner—John Sipos
Assistant Examiner—Daniel Moon
Attorney, Agent, or Firm—Herbert Dubno; Andrew Wilford

[57] ABSTRACT

An apparatus for handling a plurality of elongated tubular bodies each having a small-diameter neck and a large-diameter shaft has a pair of support plates formed with respective similar arrays of throughgoing openings generally complementary to the section of the shafts of the bodies and spacers supporting the plates parallel to and spaced from each other with the openings arranged pairwise with one opening of each plate aligned along a respective axis with a respective opening of the other plate so that the bodies can be held therein. A stop plate parallel to and spaced from the support plates is formed with stop openings in an array like the openings of the support plates. A guide supports the stop plate parallel to and at a spacing from the support plates for sliding the stop plate parallel to the support plates between a loading position with the stop-plate openings aligned axially with the support-plate openings and the syringe bodies freely axially movable through the stop-plate openings and a blocking position with the stop-plate openings bearing radially of the axes on the small-diameter necks of the syringe bodies and retaining same against axial movement in the respective openings.

14 Claims, 2 Drawing Sheets

APPARATUS FOR HANDLING SYRINGE BODIES

FIELD OF THE INVENTION

The present invention relates to the handling of syringe bodies. More particularly this invention concerns an apparatus for holding syringe bodies as they are cleaned, filled, capped, or otherwise worked on.

BACKGROUND OF THE INVENTION

In the course of the individual processing steps involved in the fabrication of syringe bodies and like injection molded articles, e.g. from the end of cleaning up to the final labelling, the syringe bodies are generally handled in randomly distributed or piled masses. This means that the syringes must be oriented again for each new process step, i.e. they must be brought into a predetermined position or orientation for further processing. Particularly in mechanical processing this takes an exceptional amount of work and requires additional mechanical devices to perform this sorting or orientation.

There are already known auxiliary devices, e.g. bucket or cup chains, suspension rails or the like, with which the finished syringe bodies can be transported and further processed. However these devices, which are comparatively expensive and troublesome, can damage the syringes. Also such devices are susceptible to breakdown and are only adjustable to changing process conditions with great difficulty, if at all.

In commonly owned U.S. Pat. No. 4,774,772 an apparatus for handling finished syringe bodies comprises a planar support plate and a mounting plate provided with foot members and connected with the support plate. This mounting plate is positioned substantially parallel to the support plate by a plurality of spacers. The support plate and the mounting plate each have a plurality of openings for receiving the finished syringe bodies. Each support-plate opening is aligned along a respective axis with a respective mounting-plate opening and all of these axes are parallel. A retaining plate is provided with holes coaxial with the receiving openings and is connected detachably to the support plate on the side of the support plate facing away from the mounting plate. The edges of the holes in the retaining plate contact the flanges of the finished syringe bodies placed in the receiving openings.

It is thus possible in this system to mount the finished syringe bodies in the device in the individual processing stations in a plurality of arrangements and orientations, even upside down, so that particularly automatic processes can be carried out without the syringe bodies falling out of the apparatus. However holes of the retaining plate allow free access to the interior of the injection molding cylinder and/or the insertion of the plungers in the syringe bodies.

The disadvantage of this system is that the retaining plate must be mounted rather carefully on the mounting and support plates. The positioning elements must be carefully aligned in order to ensure perfect alignment of the retaining-plate holes with the mouths of the syringes.

OBJECTS OF THE INVENTION

It is therefore an object of the present invention to provide an improved apparatus for handling syringe bodies.

Another object is the provision of such an improved apparatus for handling syringe bodies which overcomes the above-given disadvantages, that is which allows a group of syringe bodies to be locked in place with ease and absolute assurance of perfect alignment.

SUMMARY OF THE INVENTION

An apparatus for handling a plurality of elongated tubular bodies each having a small-diameter neck and a large-diameter shaft according to the invention has a pair of support plates formed with respective similar arrays of through-going openings generally complementary to the section of the shafts of the bodies and spacers supporting the plates parallel to and spaced from each other with the openings arranged pairwise with one opening of each plate aligned along a respective axis with a respective opening of the other plate so that the bodies can be held therein. A stop plate parallel to and spaced from the support plates is formed with stop openings in an array like the openings of the support plates. A guide supports the stop plate parallel to and at a spacing from the support plates for sliding the stop plate parallel to the support plates between a loading position with the stop-plate openings aligned axially with the support-plate openings and the syringe bodies freely axially movable through the stop-plate openings and a blocking position with the stop-plate openings bearing radially of the axes on the small-diameter necks of the syringe bodies and retaining same against axial movement in the respective openings.

Thus simply shifting the stop plate locks in or frees the ampoules or syringe bodies. This is an extremely simple movement that can easily be done by an automatic treatment machine, for instance a filling apparatus, so that manually handling or setting up the group of bodies for treatment becomes unnecessary.

According to a feature of the invention the small-diameter necks of the bodies form outwardly open recesses and the stop-plate openings have edges engaging in the recesses in the blocking position. More particularly according to this invention the holes of the stop plate are keyhole shaped and each have a small part-circular lobe of a diameter generally equal to that of the bodies at the neck and a large part-circular lobe of a diameter generally equal to that of the bodies at the shaft. In this manner an extremely solid retention of the bodies in the apparatus is certain.

In accordance with a further inventive feature the bodies are formed with radially outwardly projecting and axially elongated bypasses and the support plates are positioned such that one of them axially engages ends of the bypasses when the bodies are fitted to the holes. Thus the bodies are retained axially in one direction by engagement of the bypasses with the one support plate and in the opposite direction by engagement of the neck region with the stop plate.

Furthermore according to the invention one of the support plates is formed at each of the spacers with a foot supporting the support plate. The other of the support plates is formed with guides projecting up away from the feet past the stop plate and the apparatus also has a closing plate displaceable along the guides toward and away from the support plates and formed with seats adapted to hold caps aligned axially with the openings. Thus the closing plate is formed with blind bores in which the guides engage and compression springs are engaged in the blind bores between the closing plate and the guides. Furthermore each guide is provided with an abutment against which the closing plate is engageable and each abutment has an elastomeric cover engageable with the closing plate.

The guide controlling sliding of the stop plate according to this invention has a plurality of guide pins fixed on the support plates. The stop plate is formed with respective elongated slots through which the pins project. The pins are seated and fixed in both support plates.

BRIEF DESCRIPTION OF THE DRAWING

The above and other objects, features, and advantages will become more readily apparent from the following, reference being made to the accompanying drawing in which.

SPECIFIC DESCRIPTION

Figure 1:
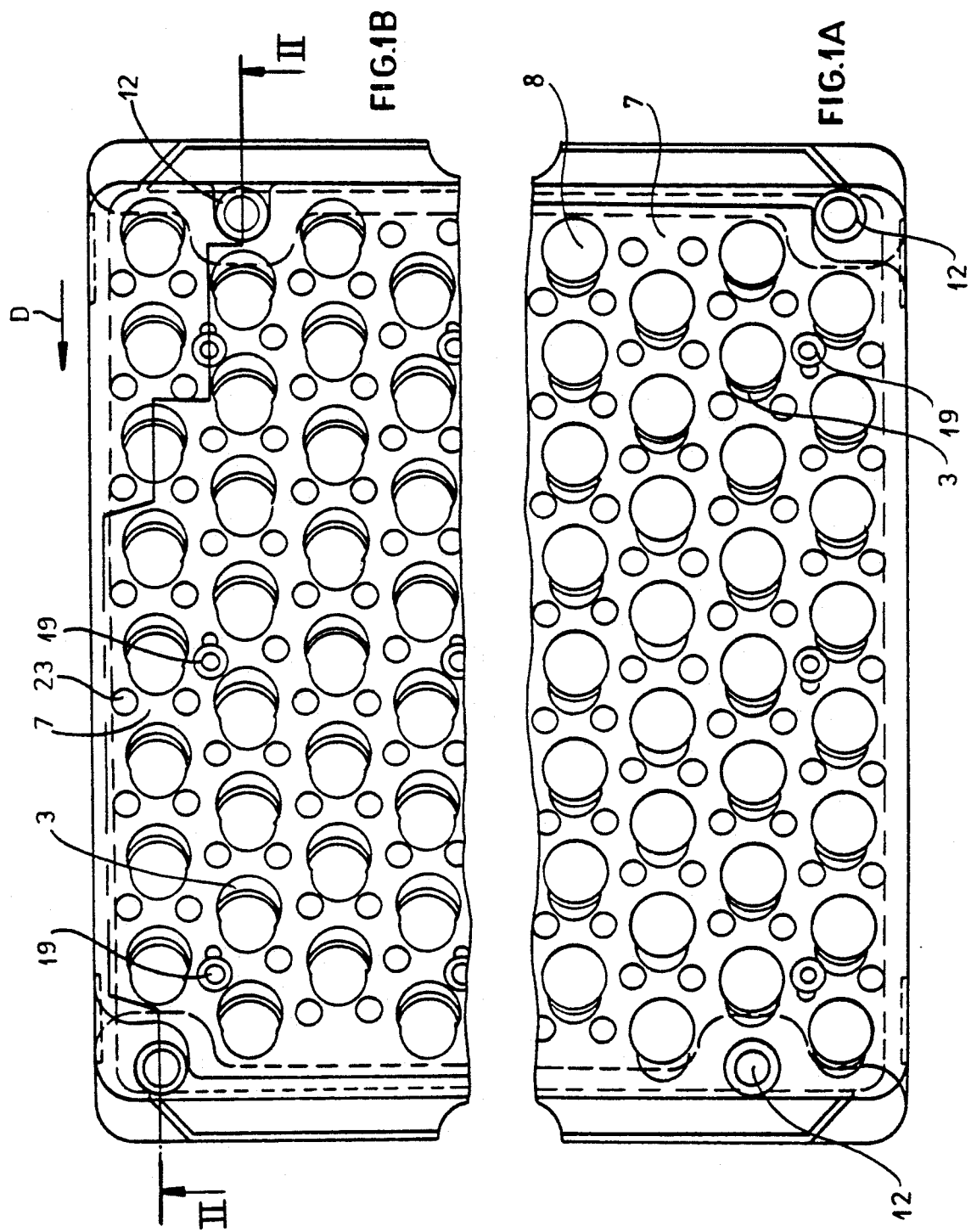
FIGS. 1A and 1B are top views of the apparatus in the loading and blocking positions, respectively.
Figure 2:
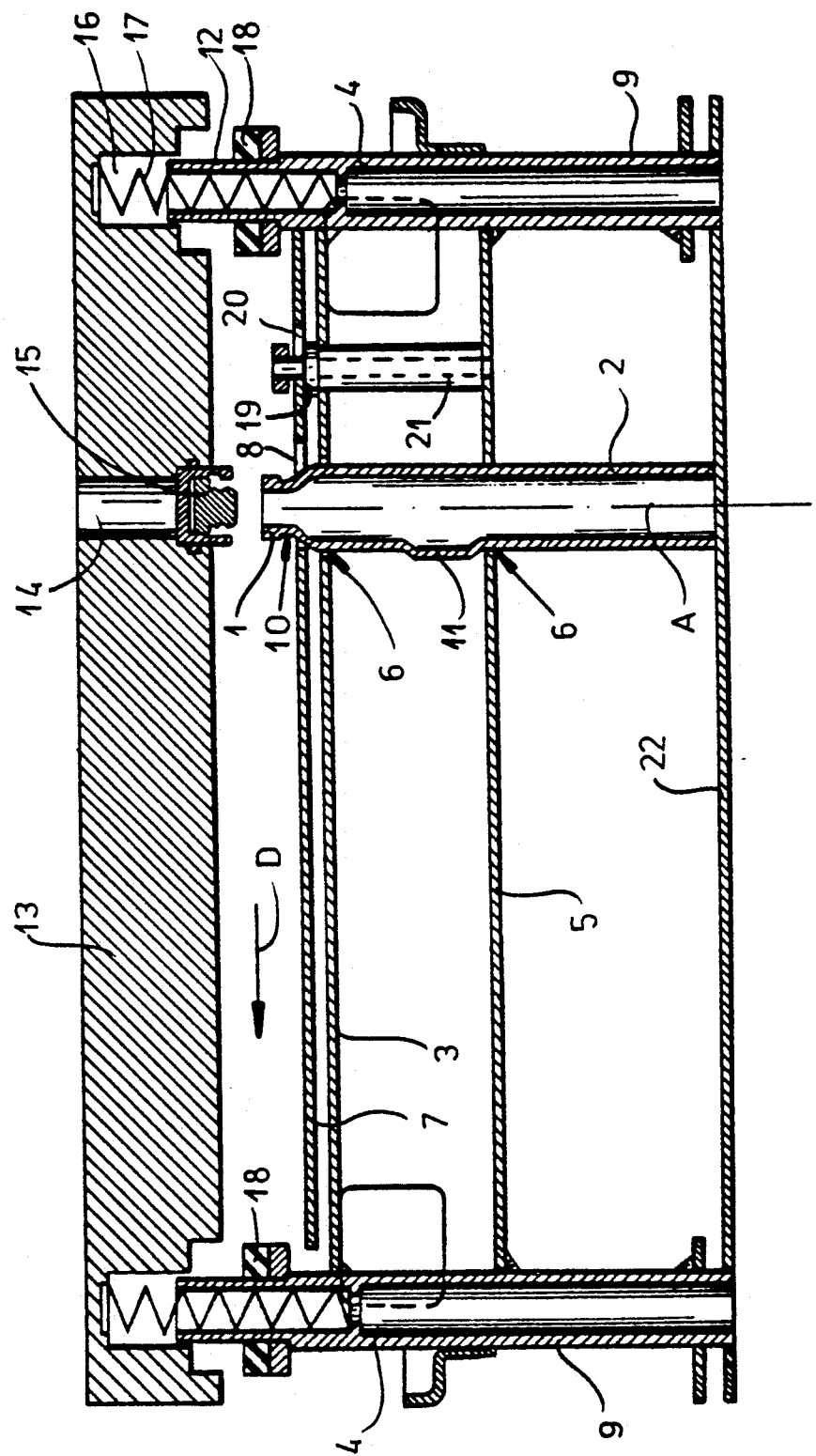
FIG. 2 is a section taken along line II—II of FIG. 1B.

As seen in FIGS. 1A, 1B, and 2 the apparatus according to this invention is used to hold a plurality of syringe bodies 2 each having a small-diameter neck 1 and a large-diameter shaft, although it is of course possible to use this apparatus with similarly shaped tubular bodies, such as ampoules. The apparatus has a planar support plate 3 held by spacers 4 above a lower adjustment plate 5 itself supported on a lowermost base plate 22 by feet 9. The plates 3 and 5 are formed with identical arrays of identical circular holes 6 arranged in pairs aligned along respective axes A perpendicular to the planes of the plates 3 and 5. The holes 6 are in diameter slightly greater than the outside diameters of the bodies 2 so that same can be fitted to them to hold these bodies 2 centered on the axes A. When the bodies 2 are formed with axially extending bypass ridges 11 of the type used in mixing syringes these ridges 11 sit at their lower ends on the plate 5 to accurately position the respective syringe bodies 2. When they have such bypasses 11, of course the holes 6 of the upper plate 3 must be enlarged or formed with cutouts to pass them.

According to this invention a stop plate 7 is formed with throughgoing keyhole-shaped holes s in an array identical to that of the holes 6 and is supported a short distance above the plate 3 so that it is level with annular outwardly open grooves or recesses 10 formed below the neck 1 of each body 2. Each hole 8 has a small part-circular lobe of a diameter equal to that of the neck 1 at the recess 10 and a large part-circular lobe of a diameter equal to that of the holes 6, with the centers of curvature of the lobes spaced apart in a direction corresponding to a direction D in which the plate 7 can be slid. To this end the plate 3 is provided with upstanding guide pins 19 that extend through slots 20 formed in the plate 7 and extending in the direction D. These pins 19 have downward extensions 21 attached to the plate 5 so that they are quite strong and stable and, indeed, they help to space the plates 3 and 5 the requisite distance from each other.

Thus it is possible to shift the plate 7 into the loading position of FIG. 1A and slide the bodies 2 down into the aligned holes 6 and 8. Once all the holes are filled, the plate 7 is then shifted to the blocking position of FIG. 1B in which the necks 1 are snugly engaged by the small-diameter lobes of the holes 8, thereby locking them axially in place. In this blocking position it is possible to invert the assembly without dropping out the bodies 2. A latch, for instance a pin insertable through aligned holes 23 in the plates 3 and 7 can be used to retain the apparatus in the blocking position.

When the bodies 2 have the bypass ridges 11, it is possible for both lobes of the holes 8 to be of the same large diameter and for the holes 8 simply to engage the bodies 2 on the upper ends of the bypasses 11. This captures the bypasses 11 between the plates 5 and 7, thereby effectively axially locking the bodies 2 in place.

Upwardly extending tubular guide sleeves 12, which are actually unitary with and extensions of the spacers 4 and feet 9 contain respective compression springs 17 having upper ends seated in downwardly open blind bores 16 of a closing plate 13. This plate 13 is formed with an array of seats 14 for closures 15. Thus pushing the plate 13 downward can simultaneously cap all the bodies 2 held in the plates 3, 5, and 7. The sleeve guides 12 carry elastomeric bumpers 18 engageable upward with the plate 13 to cushion it at the end of its downward displacement.

We claim:

1. An apparatus for handling a plurality of elongated and tubular glass syringe bodies each having
   a small-diameter neck,
   a radially outwardly projecting and axially elongated bypass, and
   a large-diameter mainly cylindrical shaft and predetermined circular section, the apparatus comprising:
   a pair of support plates formed with respective similar arrays of throughgoing openings generally complementary to the section of the shafts of the bodies, the support plates being positioned such that one of them axially engages ends of the bypasses when the bodies are fitted to the openings;
   spacers supporting the plates parallel to and spaced from each other with the openings arranged pairwise with on opening of each plate aligned along a respective axis with a respective opening of the other plate so that the bodies can be held therein;
   a stop plate parallel to and spaced from the support plates and formed with stop openings in an array substantially identical to the arrays of openings of the support plates, the stop-plate openings being substantially wider in at least one direction than the support-plate openings; and
   guide means supporting the stop plate parallel to and at a spacing from the support plates level with the small-diameter necks of the bodies when they are seated in the openings of the support plates for sliding the stop plate parallel to the support plates between
      a loading position with the stop-plate openings aligned axially with the support-plate openings and the syringe bodies freely axially movable through the stop-plate openings and
      a blocking position with the stop-plate openings hearing radially of the axes on the small-diameter necks of the syringe bodies and retaining same against axial movement in the respective openings.

2. The handling apparatus defined in claim 1 wherein the small-diameter necks of the bodies form outwardly open recesses, the stop-plate openings having edges engaging in the recesses in the blocking position.

3. The handling apparatus defined in claim 1 wherein one of the support plates is formed at each of the spacers with a foot supporting the support plate.

4. The handling apparatus defined in claim 3 wherein the other support plate is formed with guides projecting up away from the feet past the stop plate, the apparatus further comprising
   a closing plate displaceable along the guides toward and away from the support plates and formed with seats adapted to hold caps aligned axially with the openings.

5. The handling apparatus defined in claim 4 wherein the closing plate is formed with blind bores in which the guides engage.

6. The handling apparatus defined in claim 5, further comprising
   compression springs engaged in the blind bores between the closing plate and the guides.

7. The handling apparatus defined in claim 5 wherein each guide is provided with an abutment against which the closing plate is engageable.

8. The handling apparatus defined in claim 7 wherein each abutment has an elastomeric cover engageable with the closing plate.

9. The handling apparatus defined in claim 1 wherein the guide means includes a plurality of guide pins fixed on the support plates, the stop plate being formed with respective elongated slots through which the pins project.

10. The handling apparatus defined in claim 9 wherein the pins are seated and fixed in both support plates.

11. An apparatus for handling a plurality of elongated and tubular glass syringe bodies each having a small-diameter neck and a large-diameter mainly cylindrical shaft of predetermined circular section, the apparatus comprising:
   a pair of support plates formed with respective similar arrays of throughgoing openings generally complementary to the section of the shafts of the bodies;
   spacers supporting the plates parallel to and spaced from each other with the openings arranged pairwise with one opening of each plate aligned along a respective axis with a respective opening of the other plate so that the bodies can be held therein;
   a stop plate parallel to and spaced from the support plates and formed with stop openings in an array substantially identical to the arrays of openings of the support plates, the stop-plate openings being substantially wider in at least one direction than the support-plate openings, the openings of the stop plate being keyhole shaped and each having a small part-circular lobe of a diameter generally equal to that of the bodies at their necks and a large part-circular lobe of a diameter generally equal to that of the bodies at their shafts; and
   guide means supporting the stop plate parallel to and at a spacing from the support plates level with the small-diameter necks of the bodies when they are seated in the openings of the support plates for sliding the stop plate parallel to the support plates between
      a loading position with the stop-plate openings aligned axially with the support-plate openings and the syringe bodies freely axially movable through the stop-plate openings and
      a blocking position with the stop-plate openings bearing radially of the axes on the small-diameter necks of the syringe bodies and retaining same against axial movement in the respective openings.

12. The handling apparatus defined in claim 11 wherein the bodies are formed with radially outwardly projecting and axially elongated bypasses, the support plates being positioned such that one of them axially engages ends of the bypasses when the bodies are fitted to the openings.

13. An apparatus for handling a plurality of elongated and tubular glass syringe bodies each having a small-diameter neck and a large-diameter shaft of predetermined circular section, the apparatus comprising:
   a pair of support plates formed with respective similar arrays of generally circular throughgoing openings generally complementary to the section of the shafts of the bodies;
   spacers supporting the plates parallel to and spaced from each other with the openings arranged pairwise with one opening of each plate aligned along a respective axis with a respective opening of the other plate so that the bodies can be held therein;
   a stop plate parallel to and spaced from the support plates and formed with a plurality of keyhole-shaped stop openings in an array substantially identical to the arrays of openings of the support plates each stop opening having a small part-circular lobe of a diameter generally equal to that of the bodies at the neck and a large part-circular lobe of a diameter generally equal to that of the bodies at the shaft; and
   guide means supporting the stop plate parallel to and at a spacing from the support plates level with the small-diameter necks of the bodies when they are seated in the openings of the support plates for sliding the stop plate parallel to the support plates between
      a loading position with the large-diameter lobes of the stop-plate openings aligned axially with the support-plate openings and the syringe bodies freely axially movable through the stop-plate openings and
      a blocking position with the small-diameter lobes of the stop-plate openings fitting against the small-diameter necks of the syringe bodies and retaining same against axial movement in the respective openings.

14. An apparatus for handling a plurality of elongated and tubular glass syringe bodies each having a small-diameter neck, a large-diameter mainly cylindrical shaft, and a radially outwardly projecting and axially elongated bypass with axially opposite ends, the apparatus comprising:
   a pair of support plates formed with respective similar arrays of throughgoing circular openings generally complementary to the shafts of the bodies, the support plates being positioned such that one of them axially engages one end of each of the bypasses when the bodies are fitted to the openings;
   spacers supporting the plates parallel to and spaced from each other with the openings arranged pairwise with one opening of each plate aligned along a respective axis with a respective opening of the other plate so that the bodies can be held therein;
   a stop plate parallel to and spaced from the support plates and formed with stop openings in an array substantially identical to the arrays of openings of the support plates; and guide means supporting the stop plate parallel to and at a spacing from the support plates level with the small-diameter necks of the bodies when they are seated in the openings of the support plates for sliding the stop plate parallel to the support plates between a loading position with the stop-plate openings aligned axially with the support-plate openings and the syringe bodies freely axially movable through the stop-plate openings and a blocking position with the stop-plate openings bearing radially of the axes on the small-diameter necks of the syringe bodies and retaining same against axial movement in the respective openings.

* * * * *